(12) United States Patent
Lin et al.

(10) Patent No.: US 9,745,309 B2
(45) Date of Patent: Aug. 29, 2017

(54) METHOD FOR PREPARING A SITAGLIPTIN INTERMEDIATE

(71) Applicants: Zhejiang Medicine Co., Ltd. Xinchang Pharmaceutical Factory, Xinchang County (CN); SHANGHAI INSTITUTE OF PHARMACEUTICAL INDUSTRY, Shanghai (CN)

(72) Inventors: Kuaile Lin, Xinchang County (CN); Zhengyan Cai, Xinchang County (CN); Jing Pan, Xinchang County (CN); Weicheng Zhou, Xinchang County (CN); Guofeng Wu, Xinchang County (CN); Lirong Yue, Xinchang County (CN); Dadong Shen, Xinchang County (CN)

(73) Assignees: Shanghai Institute of Pharmaceutical Industry (CN); Zhejiang Medicine Co., Ltd. (CN)

( * ) Notice: Subject to any disclaimer, the term of this patent is extended or adjusted under 35 U.S.C. 154(b) by 0 days.

(21) Appl. No.: 15/021,066

(22) PCT Filed: Sep. 9, 2014

(86) PCT No.: PCT/CN2014/000832
§ 371 (c)(1),
(2) Date: Mar. 10, 2016

(87) PCT Pub. No.: WO2015/035735
PCT Pub. Date: Mar. 19, 2015

(65) Prior Publication Data
US 2016/0229859 A1    Aug. 11, 2016

(30) Foreign Application Priority Data

Sep. 10, 2013  (CN) .......................... 2013 1 0409694

(51) Int. Cl.
*C07D 487/04*        (2006.01)

(52) U.S. Cl.
CPC ........ *C07D 487/04* (2013.01); *C07B 2200/13* (2013.01)

(58) Field of Classification Search
CPC .................................................... C07D 487/04
USPC .......................................................... 544/350
See application file for complete search history.

*Primary Examiner* — Douglas M Willis
(74) *Attorney, Agent, or Firm* — William D. Hare; McNeely, Hare & War, LLP

(57) ABSTRACT

The present invention provides a method for preparing an intermediate compound of sitagliptin represented by formula I. The preparation method comprises: dissolving a compound represented by formula II into an organic solvent; and under the catalysis of fatty acid and effect of chlorosilane, performing a reduction reaction of carbon-carbon double bonds, so as to obtain the intermediate compound of sitagliptin represented by formula I, R being methyl or formoxyl. The preparation method of the present invention avoids precious metal as a catalyst, and accordingly, the cost is low, the post-treatment is simple, the product has a high yield, chemical purity and optical purity, and de % is greater than 99.6%, and the preparation method can be used in synthesis of sitagliptin and is suitable for industrial production.

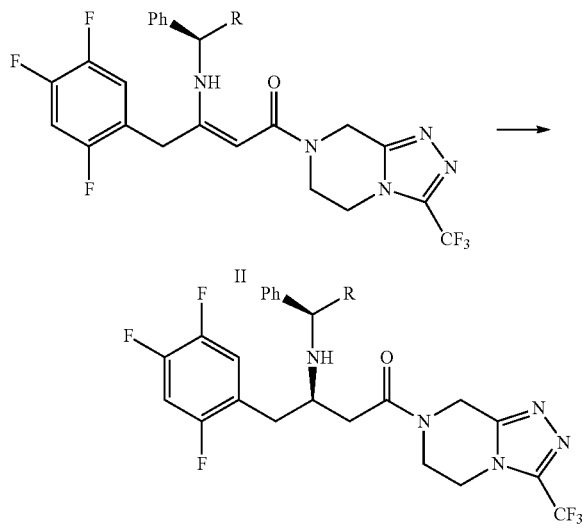

12 Claims, No Drawings

METHOD FOR PREPARING A SITAGLIPTIN INTERMEDIATE

CROSS REFERENCE TO RELATED APPLICATIONS

This application is a national phase application of PCT/CN2014/000832, filed on Sep. 9, 2014, which claims priority to Chinese Application No. 201310409694.X filed on Sep. 10, 2013.

FIELD OF THE INVENTION

The present invention relates to the field of pharmaceutical chemical synthesis, and in particular relates to a method for preparing intermediate compound of sitagliptin.

BACKGROUND OF THE INVENTION

Sitagliptin is chemically referred to as 7-[1-oxo-3R-3-amino-4-(2,4,5-trifluorophenyl)butyl]-3-trifluoromethyl-5,6,7,8-tetrahydro-1,2,4-triazolo[4,3-a]pyrazine, and is shown in formula 1. Sitagliptin is a dipeptidyl peptidase-IV (DPP-IV) inhibitor for treatment of type-II diabetes mellitus clinically developed by Merck & Co Inc.

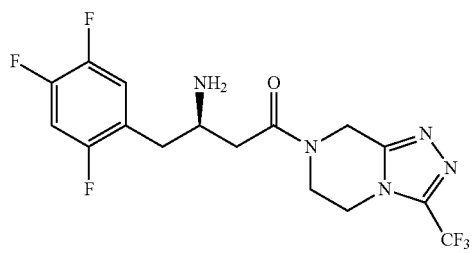

1

In the process of preparing sitagliptin, construction of chiral amino is a key point of synthetic route. The method of constructing chiral amino in the process of preparing sitagliptin is as follows:

Route I: (Reference: WO2004/085378)

In the route according to WO2004/085378, constructing chiral amino of sitagliptin is implemented by a hydrogenation reduction reaction with metal rhodium and chiral ferrocenyl diphosphine. But disadvantages of the method are increased costs and difficulty in being suitable for industrial production due to use of two expensive reagents including metal rhodium and chiral ferrocene ligand.

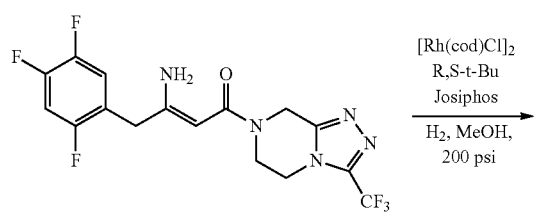

2

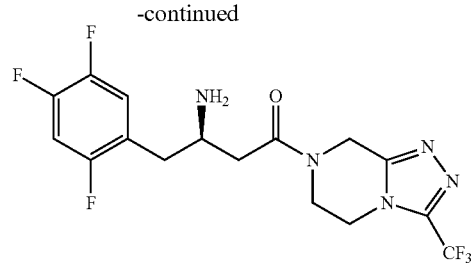

1

Route II: (Reference: WO2004/085661)

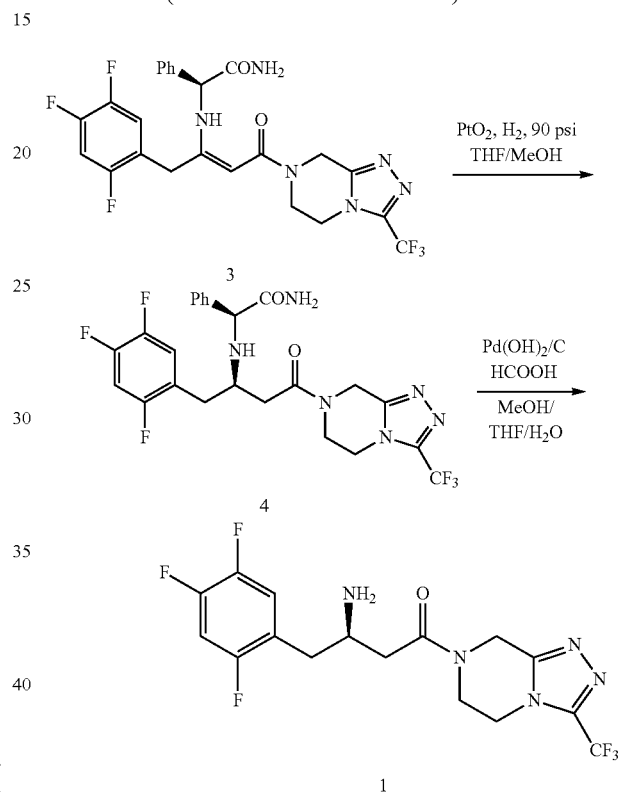

In the route according to WO2004/085661, S-benzene ammonia amide as a chiral auxiliary is introduced and conducted a catalytic hydrogenation by platinum oxide to induce the desired chiral amino, to produce sitagliptin by debenzylation. But disadvantages of the method are increased costs and difficulty in being suitable for industrial production due to use of the precious metal platinum oxide as the catalyst.

Route III: (Reference: WO2009/085990)

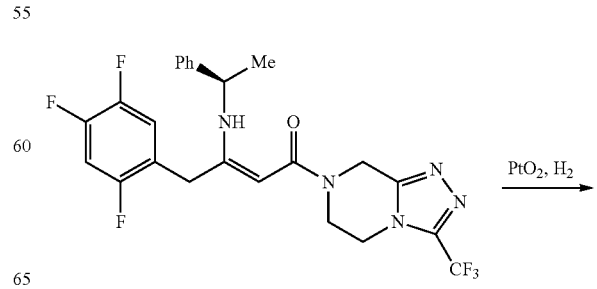

5

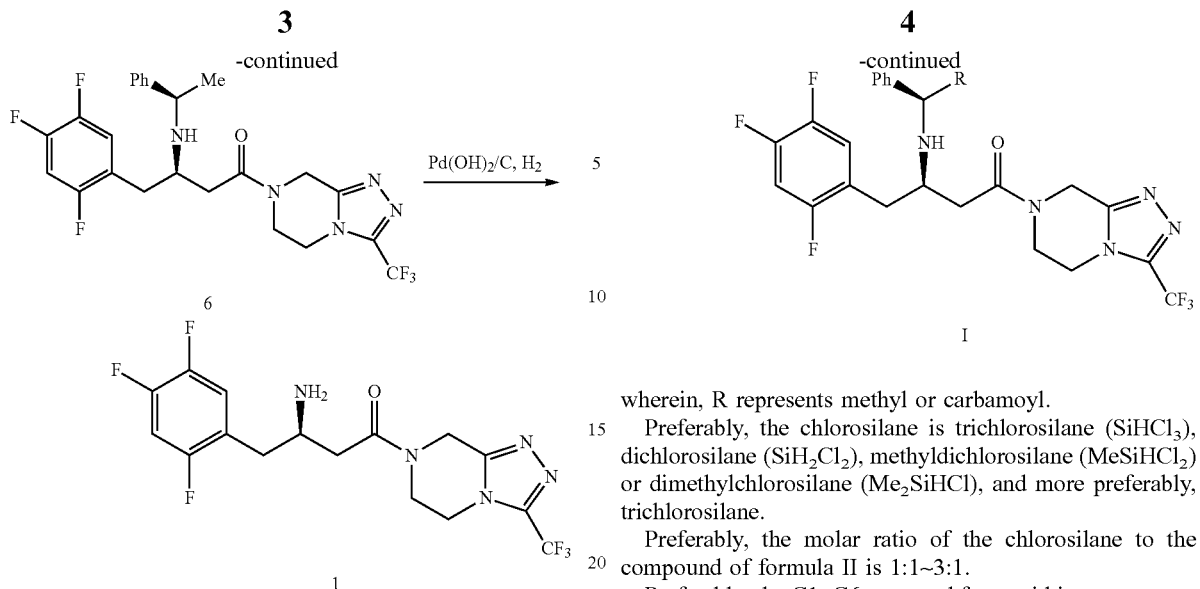

In the route according to WO2009/085990, a chiral auxiliary is R-α-methylbenzylamine instead of S-benzene ammonia amide. But the chiral amino is similarly induced by expensive platinum oxide as catalyst.

It has been reported from the prior art to use several methods for preparing sitagliptin. But they have one or more disadvantages, such as use of expensive reagents (platinum oxide, rhodium catalyst etc.), and/or addition of more protection steps. So it is necessary to develop simple and more economical synthetic routes to be suitable for industrial production.

SUMMARY OF THE INVENTION

In order to overcome the deficiencies of conventional methods of preparing intermediate of sitagliptin such as uses of expensive reagents and expensive costs and not being suitable for industrial production, the purpose of the present invention is to provide a method of preparing the intermediate compound of sitagliptin of formula I to be entirely different from that of the prior art.

In order to achieve the above purpose, the present invention provides a method of preparing intermediate compound of sitagliptin of formula I, the method comprising: dissolving a compound of formula II in an organic solvent; and performing a reduction reaction of carbon-carbon double bonds with chlorosilane under catalysis of $C_1$~$C_6$ saturated fatty acid, to produce intermediate compound of sitagliptin of formula I, the chemical reaction equation is as follows:

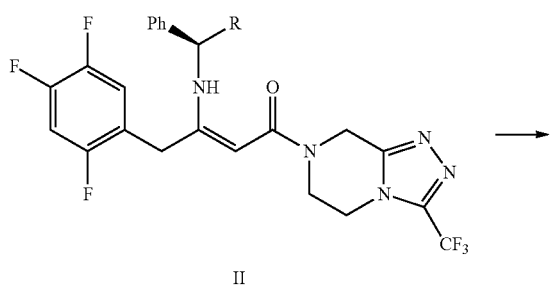

wherein, R represents methyl or carbamoyl.

Preferably, the chlorosilane is trichlorosilane ($SiHCl_3$), dichlorosilane ($SiH_2Cl_2$), methyldichlorosilane ($MeSiHCl_2$) or dimethylchlorosilane ($Me_2SiHCl$), and more preferably, trichlorosilane.

Preferably, the molar ratio of the chlorosilane to the compound of formula II is 1:1~3:1.

Preferably, the $C_1$~$C_6$ saturated fatty acid is one or more of formic acid, acetic acid, trifluoroacetic acid, propionic acid or butyric acid, and more preferably acetic acid.

Preferably, the molar ratio of the $C_1$~$C_6$ saturated fatty acid to the compound of formula II is 0.5:1~1.5:1.

Preferably, the organic solvent is selected from the group consisting of one or more of toluene, tetrahydrofuran, methyl tert-butyl ether, ethyl acetate and acetonitrile, more preferably toluene.

Preferably, the amount of the organic solvent is amounts of conventional chemical reaction, and the volume-to-mass ratio of the organic solvent to the compound of formula II is preferably 5~10 mL/g.

Preferably, the temperature of the reduction reaction is 0° C.~30° C., more preferably 20~30° C., most preferably 25° C. The reduction reaction time is determined by conventional test means, typically 1~24 hours.

In the present invention, each of conditions of the reduction reaction can be conducted in accordance with conventional conditions of reduction reaction in the field, besides specifically described above.

After completing the reduction reaction, the intermediate compound of sitagliptin as shown in formula I can be obtained by simple post-processing such as cancellation, extraction, washing, drying, and/or concentration.

Preferably, the method also comprises crystallization of the intermediate compound of sitagliptin as shown in formula I from alcohol(s) and a mixture of alcohols with alkanes Preferably, the alcohol(s) is methanol, ethanol or isopropanol, and the alkane is petroleum ether, n-hexane or n-heptane.

The intermediate compound of sitagliptin as shown in formula I can be prepared by methods of debenzylation, for example, refer to methods of preparing sitagliptin described in route II or route III of the background of the present invention, or refer to methods of preparing sitagliptin described in WO2004/085378.

The compound of formula II of the present invention also can be prepared by the prior art, for example, the compound can be prepared by methods of WO2004/085378, wherein R in the compound of formula II is carbamoyl, and the compound can be prepared by the method of WO2009/085990, wherein R of the compound of formula II is methyl.

Advantages of the method of the present invention are to avoid precious metal as catalyst, low costs, simple posttreatments, high yields, high chemical purity and optical purity, de % of greater than 99.6%, and suitable for industrial production.

DETAILED DESCRIPTION

Hereafter, the present invention will be described specifically with reference to examples. The examples are given only for illustration of the technical solution of the present invention and should not be construed to limit the present invention.

In the present invention, de % represents diastereomer excess, that is, an absolute value by subtracting an amount of another diastereomer from an amount of diastereomer, and then divided by a sum of the two amounts. It is generally defined as follows: de %=(an amount of diastereomer a–an amount of diastereomer b)/(an amount of diastereomer a+an amount of diastereomer b).

In the present invention, ee % represents enantiomeric excess, which represents the "excess" of one enantiomer over another enantiomer, generally defined as follows: ee %=a percentage of enantiomer a–a percentage of enantiomer b.

The above preferred conditions can be combined to obtain more embodiments of the present invention without prejudice to common knowledge in the field.

The reagents and materials used in the present invention are commercially available unless otherwise indicated.

Example 1

Preparation of 7-[1-oxo-3R-3-(1R-1-phenylethyl-amino)-4-(2,4,5-trifluorophenyl) butyl]-3-trifluoromethyl-5,6,7,8-tetrahydro-1,2,4-triazolo[4,3-a]pyrazine (R of Compound of Formula I is Methyl)

Acetic acid (0.97 g, 16.2 mmol) and trichlorosilane (4.4 g, 32.4 mmol) are added to 7-[1-oxo-3-(1R-1-phenylethyl-amino)-4-(2,4,5-trifluorophenyl) butyl-2-alkenyl]-3-trifluoromethyl-5,6,7,8-tetrahydro-1,2,4-triazolo[4,3-a]pyrazine (R of compound of formula II is methyl) (8.27 g, 16.2 mmol) dissolved in tetrahydrofuran (41 mL) and methyl t-butyl ether (41 mL), and stirred overnight at 0° C., adjust pH to neutral with saturated aqueous sodium bicarbonate solution, then 100 mL ethyl acetate is added and separated, an aqueous layer is extracted with ethyl acetate for three times, washed with saturated solution of NaCl to neutral, dried with anhydrous sodium sulfate, and concentrated to produce an oily substance, isopropanol (16 mL) is added and then refluxed to produce a clear solution, cooled slowly for crystallization, filtered to produce 6.20 g product with yield of 75.0%, purity of greater than 99.5%, and de % of greater than 99.5%. Melting points: 132-134° C. MS(ES+): m/z 512 (M+H). $^1$H-NMR (CD$_3$CN): δ 1.13 (m, 3H), 2.45 (m, 1H), 2.61 (m, 3H), 2.95 (m, 1H), 3.78 (m, 2H), 3.96 (m, 2H), 4.08 (s, 1H), 4.85 (m, 2H), 7.00 (m, 4H), 7.14 (m, 3H).

Example 2

Preparation of 7-[1-oxo-3R-3-(1R-1-phenylethyl-amino)-4-(2,4,5-trifluorophenyl)butyl]-3-trifluoromethyl-5,6,7,8-tetrahydro-1,2,4-triazolo[4,3-a]pyrazine (R of Compound of Formula I is Methyl)

Formic acid (0.72 g, 15.7 mmol) and dichlorosilane (4.3 g, 31.4 mmol) are added to 7-[1-oxo-3-(1R-1-phenylethyl-amino)-4-(2,4,5-trifluorophenyl) but-2-alkenyl]-3-trifluoromethyl-5,6,7,8-tetrahydro-1,2,4-triazolo[4,3-a]pyrazine (R of compound of formula II is methyl) (8.00 g, 15.7 mmol) dissolved in tetrahydrofuran (40 mL), and stirred overnight at 20° C., adjust pH to neutral with saturated aqueous sodium bicarbonate solution, 100 mL ethyl acetate is added and separated, an aqueous layer is extracted with ethyl acetate for three times, washed with saturated solution of NaCl to neutral, dried with anhydrous sodium sulfate, and concentrated to produce an oily substance, ethanol (16 mL) is added and then refluxed to produce a clear solution, n-heptane (32 mL) is added, cooled slowly for crystallization, filtered to produce 5.70 g product with a yield of 71.0%, purity of greater than 99.5%, and a de % of greater than 99.5%. Melting points: 132-134° C.

Example 3

Preparation of 7-[1-oxo-3R-3-(1R-1-phenylethyl-amino)-4-(2,4,5-trifluorophenyl)butyl]-3-trifluoromethyl-5,6,7,8-tetrahydro-1,2,4-triazolo[4,3-a]pyrazine (R of Compound of Formula I is Methyl)

Trifluoroacetic acid (0.93 g, 8.1 mmol) and trichlorosilane (2.2 g, 16.2 mmol) are added to 7-[1-oxo-3-(1R-1-phenyl-ethylamino)-4-(2,4,5-trifluorophenyl) butyl-2-alkenyl]-3-trifluoromethyl-5,6,7,8-tetrahydro-1,2,4-triazolo[4,3-a] pyrazine (R of compound of formula II is methyl) (8.27 g, 16.2 mmol) dissolved in the toluene (58 mL), and stirred overnight at 25° C., adjust pH to neutral with saturated aqueous sodium bicarbonate solution, 100 mL ethyl acetate is added and separated, an aqueous layer is extracted with ethyl acetate for three times, washed with saturated solution of NaCl to neutral, dried with anhydrous sodium sulfate, and concentrated to produce an oily substance, isopropanol (16 mL) is added and then refluxed to produce a clear solution, petroleum ether (32 mL) is added, cooled slowly for crystallization, filtered to produce 6.05 g product with yield of 73.2%, purity of greater than 99.5%, and a de % of greater than 99.5%. Melting points: 132-134° C.

Example 4

Preparation of 7-[1-oxo-3R-3-(1S-1-phenyl-1-carbamoylmethylamino)-4-(2,4,5-trifluorophenyl)butyl]-3-trifluoromethyl-5,6,7,8-tetrahydro-1,2,4-triazolo[4,3-a]pyrazine (R of Compound of Formula I is Carbamoyl)

Propanoic acid (1.44 g, 19.5 mmol) and methyldichlorosilane (2.99 g, 260 mmol) are added to 7-[1-oxo-3-(1S-1-phenyl-1-carbamoylmethylamino)-4-(2,4,5-trifluorophenyl) butyl-2-alkenyl]-3-trifluoromethyl-5,6,7,8-tetrahydro-1,2,4-triazolo[4,3-a]pyrazine (R of compound of formula II is carbamoyl) (7.00 g, 13.0 mmol) dissolved in ethyl acetate (49 mL), and stirred overnight at 30° C., adjust pH to neutral with saturated aqueous sodium bicarbonate solution, 100 mL ethyl acetate is added and separated, an aqueous layer is extracted with ethyl acetate for three times, washed with saturated solution of NaCl to neutral, dried with anhydrous sodium sulfate, and concentrated to produce an oily substance, methanol (14 mL) is added and then refluxed to produce a clear solution, n-hexane (28 mL) is added, cooled slowly for crystallization, filtered to produce 5.06 g product with a yield of 72.0%, purity of greater than 99.5%, and a de % of greater than 99.5%. Melting points: 206-208° C. MS(ES+): m/z 541 (M+H). $^1$H-NMR (CD$_3$CN): δ 2.54 (m, 2H), 2.75 (m, 2H), 3.15 (m, 1H), 3.92 (m, 2H), 4.06 (m, 2H), 4.30 (d, 1H), 4.87 (m, 2H), 7.10 (m, 4H), 7.21 (m, 3H).

Example 5

Preparation of 7-[1-oxo-3R-3-(1S-1-phenyl-1-carbamoylmethylamino)-4-(2,4,5-trifluorophenyl)butyl]-3-trifluoromethyl-5,6,7,8-tetrahydro-1,2,4-triazolo[4,3-a]pyrazine (R of Compound of Formula I is Carbamoyl)

Butyric acid (1.71 g, 19.5 mmol) and dimethylchlorosilane (2.46 g, 26.0 mmol) are added to 7-[1-oxo-3-(1S-1-phenyl-1-carbamoylmethylamino)-4-(2,4,5-trifluorophenyl)butyl-2-alkenyl]-3-trifluoromethyl-5,6,7,8-tetrahydro-1,2,4-triazolo[4,3-a]pyrazine (R of compound of formula II is carbamoyl) (7.00 g, 13.0 mmol) dissolved in acetonitrile (35 mL) and toluene (35 mL), and stirred overnight at 20° C., adjust pH to neutral with saturated aqueous sodium bicarbonate solution, 100 mL ethyl acetate is added and separated, an aqueous layer is extracted with ethyl acetate for three times, washed with saturated solution of NaCl to neutral, dried with anhydrous sodium sulfate, and concentrated to produce an oily substance, isopropanol (14 mL) is added to obtain a mixture, and then refluxed to produce a clear solution, n-heptane (28 mL) is added, cooled slowly for crystallization, filtered to produce 5.20 g product with yield of 74.0%, purity of greater than 99.5%, and a de % of greater than 99.5%. Melting points: 206-208° C.

Example 6

Preparation of 7-[1-oxo-3R-3-amino-4-(2,4,5-trifluorophenyl)butyl]-3-trifluoromethyl-5,6,7,8-tetrahydro-1,2,4-triazolo[4,3-a]pyrazine (Sitagliptin)

Acetic acid (0.88 g, 14.68 mmol) and 20% palladium hydroxide on carbon (0.9 g, 10% wt) are added to 7-[1-oxo-3R-3-(1R-1-phenylethylamino)-4-(2,4,5-trifluorophenyl)butyl]-3-trifluoromethyl-5,6,7,8-tetrahydro-1,2,4-triazolo[4,3-a]pyrazine (R of compound of formula I is carbamoyl) (3.000 g, 5.56 mmol) dissolved in methanol (30 mL) and water (3 mL), and then pressurized with hydrogen up to 1.0 MPa, at 50° C. for 14 hours for the reaction to produce a mixture, and then the mixture is filtered to remove catalyst, and concentrated to obtain 1.92 g solid with yield of 85.0%, purity of greater than 99.5%, and an ee % of greater than 99.5%. Melting points: 118-120° C. MS(ES+): m/z 408 (M+H). $^1$H-NMR (CDCl$_3$): δ 2.48 (m, 2H), 2.73 (m, 2H), 3.56 (m, 1H), 4.08 (m, 4H), 4.94 (m, 2H), 6.90 (m, 1H), 7.07 (m, 1H).

Example 7

Preparation of 7-[1-oxo-3R-3-amino-4-(2,4,5-trifluorophenyl)butyl]-3-trifluoromethyl-5,6,7,8-tetrahydro-1,2,4-triazolo[4,3-a]pyrazine (Sitagliptin)

Acetic acid (0.88 g, 14.68 mmol) and 10% palladium on carbon (0.9 g, 10% wt) are added to 7-[1-oxo-3R-3-(1R-1-phenylethylamino)-4-(2,4,5-trifluorophenyl) butyl]-3-trifluoromethyl-5,6,7,8-tetrahydro-1,2,4-triazolo[4,3-a]pyrazine (R of compound of formula I is t methyl) (3.000 g, 5.87 mmol) dissolved in methanol (30 mL) and water (3 mL), and then pressurized with hydrogen up to 1.0 MPa, at 50° C. for 14 hours for the reaction to produce a mixture, and then the mixture is filtered to remove catalyst, and concentrated to obtain 1.94 g solid with a yield of 81.2%, a purity of greater than 99.5%, and an ee % of greater than 99.5%. Melting points: 118-120° C. MS(ES+): m/z 408 (M+H). $^1$H-NMR (CDCl$_3$): δ 2.48 (m, 2H), 2.73 (m, 2H), 3.56 (m, 1H), 4.08 (m, 4H), 4.94 (m, 2H), 6.90 (m, 1H), 7.07 (m, 1H).

The present invention is illustrated by the above examples, however, one should understand that the present invention is not limited to specific instance and implementation scheme described here. These specific examples and implementation plans are aimed at helping the person skilled in the art to practice the present invention. The persons skilled in the art is easily able from the spirit and scope of the present invention to further improve and perfect, so the present invention only restricts by the content and scope of the claims of the present invention, and its intention to cover all in the alternative solutions and equivalent solutions which are included in the appended claims, limit within the scope of the invention spirit.

We claim:
1. A method for preparing a compound of formula I:

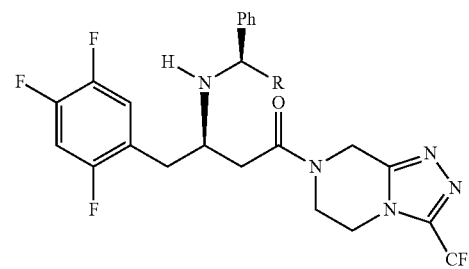

wherein R is —CH$_3$ or —CONH$_2$,
comprising the steps of:
(i) dissolving a compound of formula II:

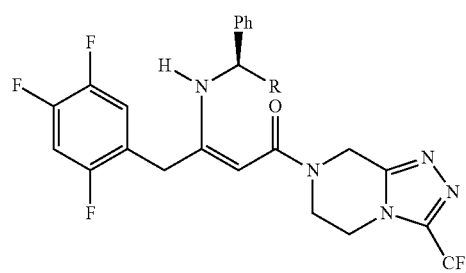

wherein R is —CH$_3$ or —CONH$_2$,
in an organic solvent; and
(ii) reducing the compound of formula II above with at least one chlorosilane of the formula:

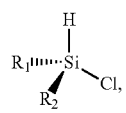

wherein R$_1$ and R$_2$ are independently —H, —Cl or —CH$_3$,
in the presence of a C1-C6 saturated fatty acid catalyst to produce the compound of formula I.

2. The method of claim 1, wherein the organic solvent is selected from the group consisting of toluene, tetrahydrofuran, methyl tert-butyl ether, ethyl acetate and acetonitrile, or a mixture thereof.

3. The method of claim 1, wherein the volume-to-mass ratio of the organic solvent to the compound of formula II is in the range of 5 mL/g to 10 mL/g.

4. The method of claim 1, wherein the chlorosilane is selected from the group consisting of trichlorosilane, methyldichlorosilane, dichlorosilane and dimethylchlorosilane, or a mixture thereof.

5. The method of claim 4, wherein the molar ratio of the chlorosilane to the compound of formula II is in the range of 1:1 to 3:1.

6. The method of claim 1, wherein the C1-C6 saturated fatty acid catalyst is selected from the group consisting of formic acid, acetic acid, trifluoroacetic acid, propionic acid and butyric acid, or a mixture thereof.

7. The method of claim 6, wherein the molar ratio of the C1-C6 saturated fatty acid catalyst to the compound of formula II is in the range of 0.5:1 to 1.5:1.

8. The method of claim 1, wherein step (ii) is conducted at a temperature in the range of 0° C. to 30° C.

9. The method of claim 1, wherein step (ii) is conducted at a temperature in the range of 20° C. to 30° C.

10. The method of claim 1, wherein step (ii) is conducted at a temperature of 25° C.

11. The method of claim 1, wherein the method further comprises crystallizing the compound of formula I from an organic solvent selected from the group consisting of an alcohol and an alkane, or a mixture thereof.

12. The method of claim 11, wherein the organic solvent is selected from the group consisting of methanol, ethanol, isopropanol, n-hexane, n-heptane and petroleum ether, or a mixture thereof.

* * * * *